(12) United States Patent
Liu et al.

(10) Patent No.: US 7,305,997 B2
(45) Date of Patent: Dec. 11, 2007

(54) DENTAL FLOSS HOLDER

(76) Inventors: Nickolas Liu, No. 50-1, Lane 232, Hulin St., ShinYi District, Taipei City 105 (TW); Ivy Wang, No. 1096, Sec. 1, Zhongshan Rd., Dajia Town, Taichung County 437 (TW)

( * ) Notice: Subject to any disclaimer, the term of this patent is extended or adjusted under 35 U.S.C. 154(b) by 369 days.

(21) Appl. No.: 11/138,367

(22) Filed: May 27, 2005

(65) Prior Publication Data

US 2006/0266378 A1  Nov. 30, 2006

(51) Int. Cl.
*A61C 15/00* (2006.01)

(52) U.S. Cl. ...................................... 132/325

(58) Field of Classification Search ......... 132/323–329
See application file for complete search history.

(56) References Cited

U.S. PATENT DOCUMENTS 4,245,658 A * 1/1981 Lecouturier ................. 132/322
5,038,806 A * 8/1991 Ewald ......................... 132/325
5,613,508 A * 3/1997 Bushman ..................... 132/325
6,474,347 B1 * 11/2002 Hallinder et al. ........... 132/325

* cited by examiner

*Primary Examiner*—Cris Rodriguez
*Assistant Examiner*—Rachel A. Running
(74) *Attorney, Agent, or Firm*—Troxell Law Office, PLLC

(57) ABSTRACT

A dental floss holder for storing and manipulating dental floss used for cleaning a person's teeth comprises a housing, a spool, a fork, a bottom board, a fasten wheel, a block member, a sleeve, a retrieving wheel, a retaining portion and a roll of dental floss which is reeled in the spool, wherein the housing has a position base and an assembling zone at two ends thereof being opposite to each other. The fork is fitted on the position base, the block member is assembled on the housing, the retaining portion is assembled on the bottom board, and the spool, the fasten wheel, the retrieving wheel, the sleeve are defined to coaxially assemble with the assembling zone.

15 Claims, 7 Drawing Sheets

DENTAL FLOSS HOLDER

BACKGROUND OF THE INVENTION

1. Field of the Invention

The present invention relates to devices for storing and manipulating dental floss used for cleaning a person's teeth, particularly to an improved dental floss holder manipulated in mechanical means to tighten up dental floss or to replace, and the dental floss holder can be used repeatedly.

2. Related Art

As is well known, oral hygiene is very important. A basic approach to maintain a well oral hygiene is to brush teeth after every meal. However, it is difficult to brush teeth everywhere after a meal and is not easy to scale the teeth by brushing. Therefore, for the importance of oral hygiene, dentists appeal to everyone to brush teeth cooperatively with picking teeth by dental floss. Conventional dental floss holder is generally classified to two types: one is spooling type and the other one is Y-shaped type; dental floss of the preceding type is reeled in paper spool, when use, users have to draw the floss and tighten the floss up to scale teeth; in this way to clean teeth particularly requires cleanness of hands, or oral hygiene may be affected; besides rear molar teeth are difficult to clean in this way since manipulation angles.

As to the Y-shaped dental floss holder, dental floss thereof has been fixed on a gap of the Y-shaped holder, when use, users only need use one hand to manipulate it, therefore, the hand will not touch floss directly. However, rear molar teeth are still hard to clean due to the manipulation angles problem. Furthermore, the Y-shaped dental floss holder is usually thrown away after cleaning, which may cause garbage pollution and waste resources; so, aforementioned two types of dental floss holder need to be improved.

SUMMARY OF THE INVENTION

Accordingly, an object of the present invention is to provide a dental floss holder for easily manipulating, replacing dental floss and repeatedly use.

Further object of the present invention is to provide a dental floss holder, which enables users to adjust proper angle to clean rear molar teeth and keep well oral hygiene.

To achieve the above-mentioned objects, a dental floss holder comprises a housing, a spool, a fork, a bottom board, a fasten wheel, a block member, a sleeve, a retrieving wheel, a retaining portion and a roll of dental floss which is reeled in the spool, wherein the housing has a position base and an assembling zone at two ends thereof being opposite to each other. The fork is fitted on the position base, the block member is assembled on the housing, the retaining portion is assembled on the bottom board, and the spool, the fasten wheel, the retrieving wheel, the sleeve are defined to coaxially assemble with the assembling zone.

DESCRIPTION OF THE PREFERRED EMBODIMENTS

Figure 1:
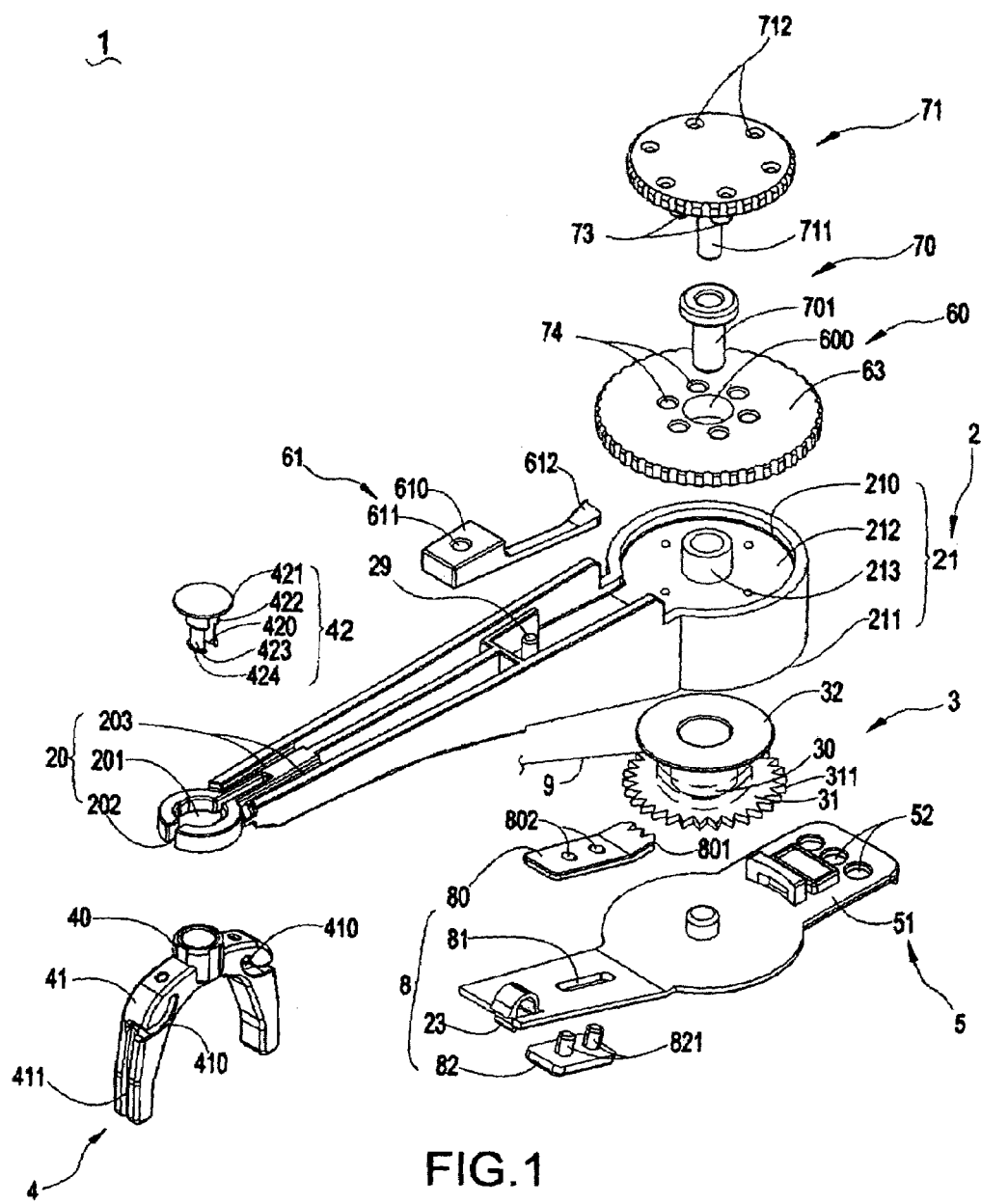
FIG. 1 is an exploded perspective view of a dental floss holder of the present invention.
Figure 2:
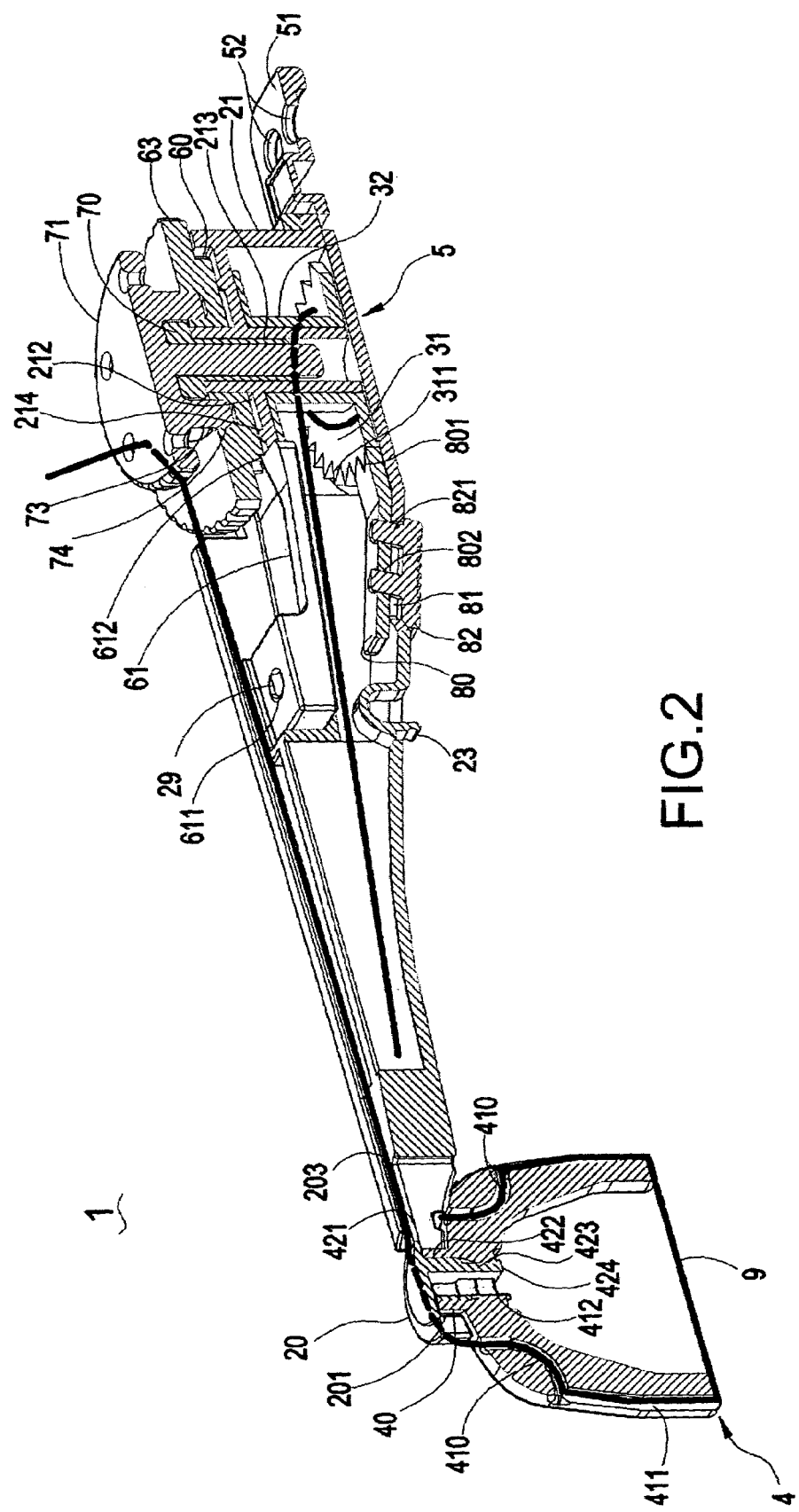
FIG. 2 is a transverse cross-sectional view of FIG. 1 being assembled.
Figure 3:
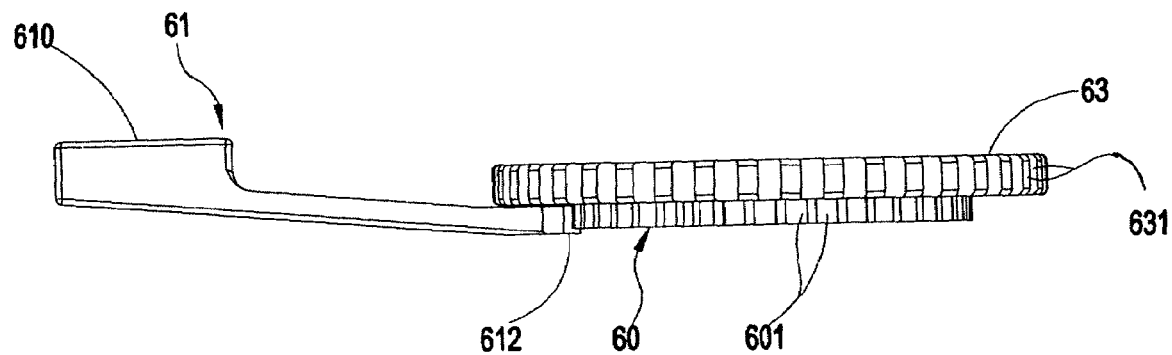
FIG. 3 is a plan view when a block member engaged with a fasten wheel.
Figure 4:
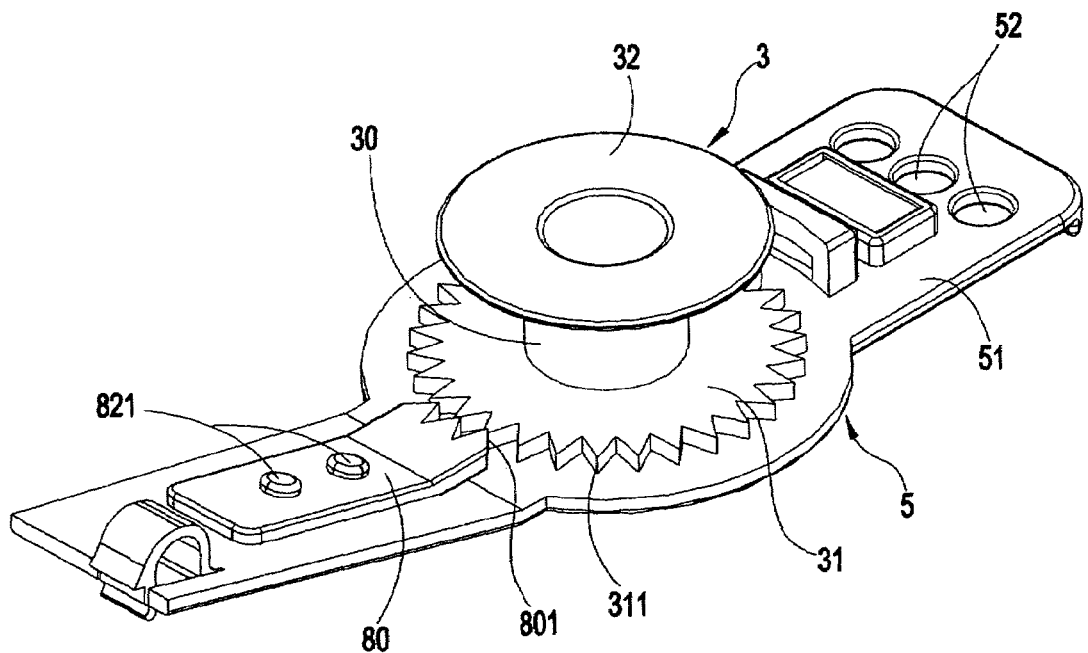
FIG. 4 and FIG. 5 are perspective views of a process of a spool engaged with a retaining portion.
Figure 5:
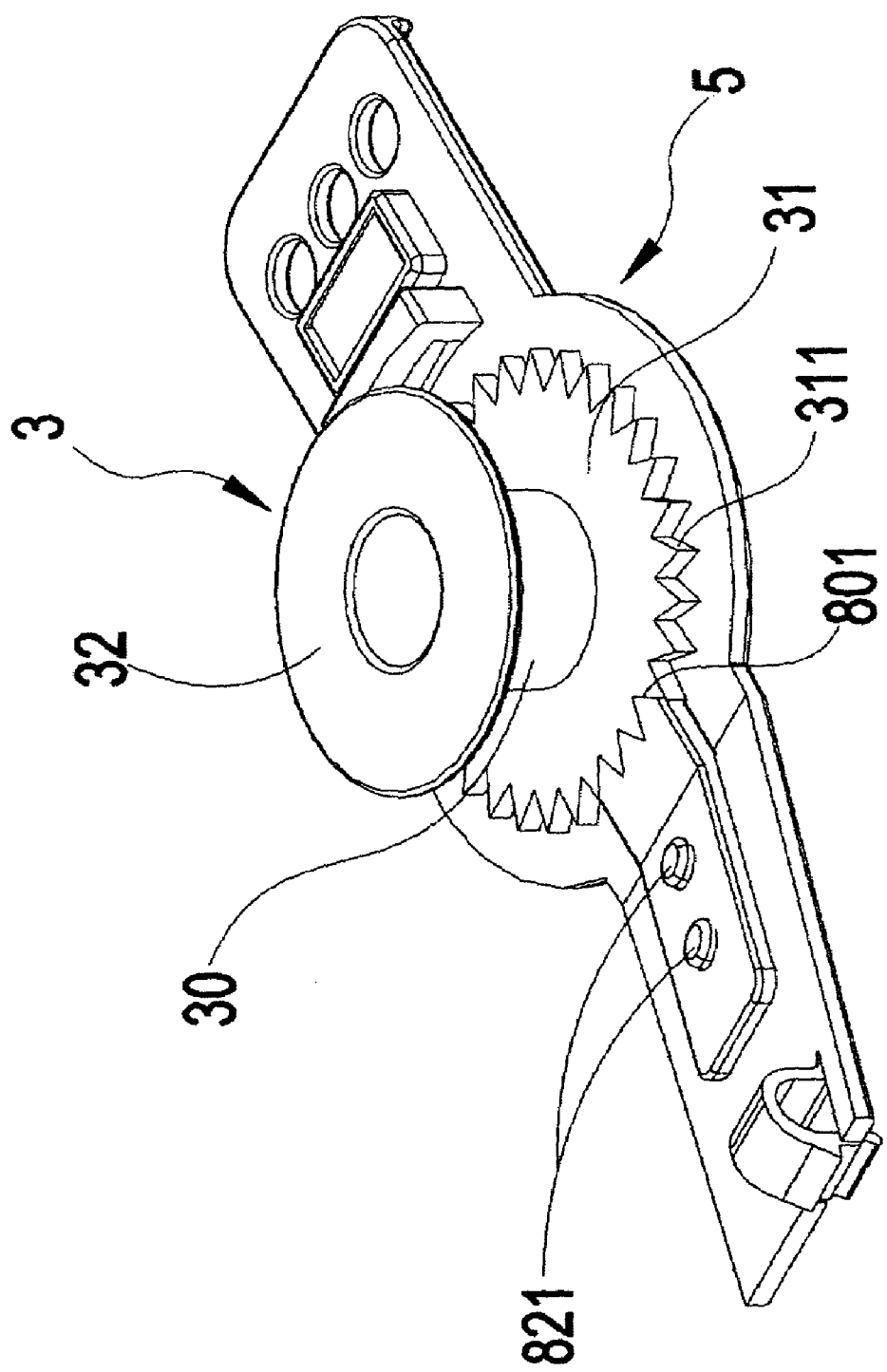

With reference to FIGS. 1 and 2, a dental floss holder 1 comprises: a housing 2, a spool 3, a fork 4, a bottom board 5, a fasten wheel 60, a block member 61, a sleeve 70, a retrieving wheel 71, a retaining portion 8 and a roll of dental floss 9, wherein the housing 2 being substantially rectangle has a position base 20 at an end thereof and an assembling zone 21 at another end opposite to the position base 20. The position base 20 unitarily and horizontally extends from an end of the housing 2 being annular and defines an annular aperture 201 therein and forms a gap 202 thereon being located through the annular aperture 201 for providing the position base 20 with elasticity. Furthermore, leading holes 203 are defined positioned apart at two sides of the housing 2 and opposite to the gap 202 for leading the floss 9 threading over.

The assembling zone 21 being defined interior hollow forms an upper opening 210 and a lower opening 211, wherein the lower opening 211 is covered by a bottom board 5. A partition 212 being defined inside the assembling zone 21 has a hollow column 213 thereon. The hollow column 213 is defined transversely perforating the partition 212, wherein the partition 212 further has protrusions 214 on a side of the upper opening 210.

The spool 3 includes a central tube 30, a serrated wheel 31 and a tray 32 for reeling a roll of dental floss 9, which is pivotally mounted to the hollow column 213 and adjacent to the lower opening 211. The serrated wheel 31 having zigzag recesses 311 on peripheral sides thereof is defined positioned at a side of the central tube 30 being adjacent to the bottom board 5. The tray 32 is located on a side of the central tube 30 opposite to the serrated wheel 31.

The fasten wheel 60 is positioned at a side of the central tube 30 being adjacent to the upper opening 21 having grooves 601 on peripheral sides thereof, and unitarily forms a driving plate 63 there above. The driving plate 63 has a larger diameter than the fasten wheel 60 and has ribs 631 on peripheral sides thereof for turning the fasten wheel 60.

The block member 61 has an opening 611 on the face 610 thereof wherein the opening is fixed to the housing by a peg 29 and the opposite end 612 is a pawl that sticks to the fasten wheel 60 for forcing the fasten wheel 60 only to turn in one direction.

The retaining portion 8 abutting on the assembling zone 21 of the housing 2 for controlling wheeling of the spool 3 comprises a slidable plate 80, a flute 81 and fixing plate 82. The slidable plate 80 has at least one location hole 802 thereon and defines saw teeth 801 at an end thereof for engaging with the serrated wheel 31. The flute 81 is positioned on the bottom board 5. The fixing plate 82 has a peg 821 being mounted to the location hole 802 through the flute 81 to fit together with the slidable plate 80 for transversely moving through the flute 81. Referring to FIG. 2 to FIG. 5, when the fixing plate 82 move to the serrated wheel 31, the slidable plate 80 will hit the zigzag recesses 311 becoming an engagement with serrated wheel 31 (shown as FIG. 5), therefore, the spool 3 is retained by the engagement. Namely, when use the dental floss holder 1, the spool 3 is retained to prevent the dental floss 9 being loose. When fixing plate 82 moves in reverse, the saw teeth 801 of the slidable plate 80 disengages from the zigzag recesses 311 of the serrated wheel 31 (shown as FIG. 4), therefore, the spool 3 reverts to be available, and the floss 9 can be drawn at will.

Figure 7:
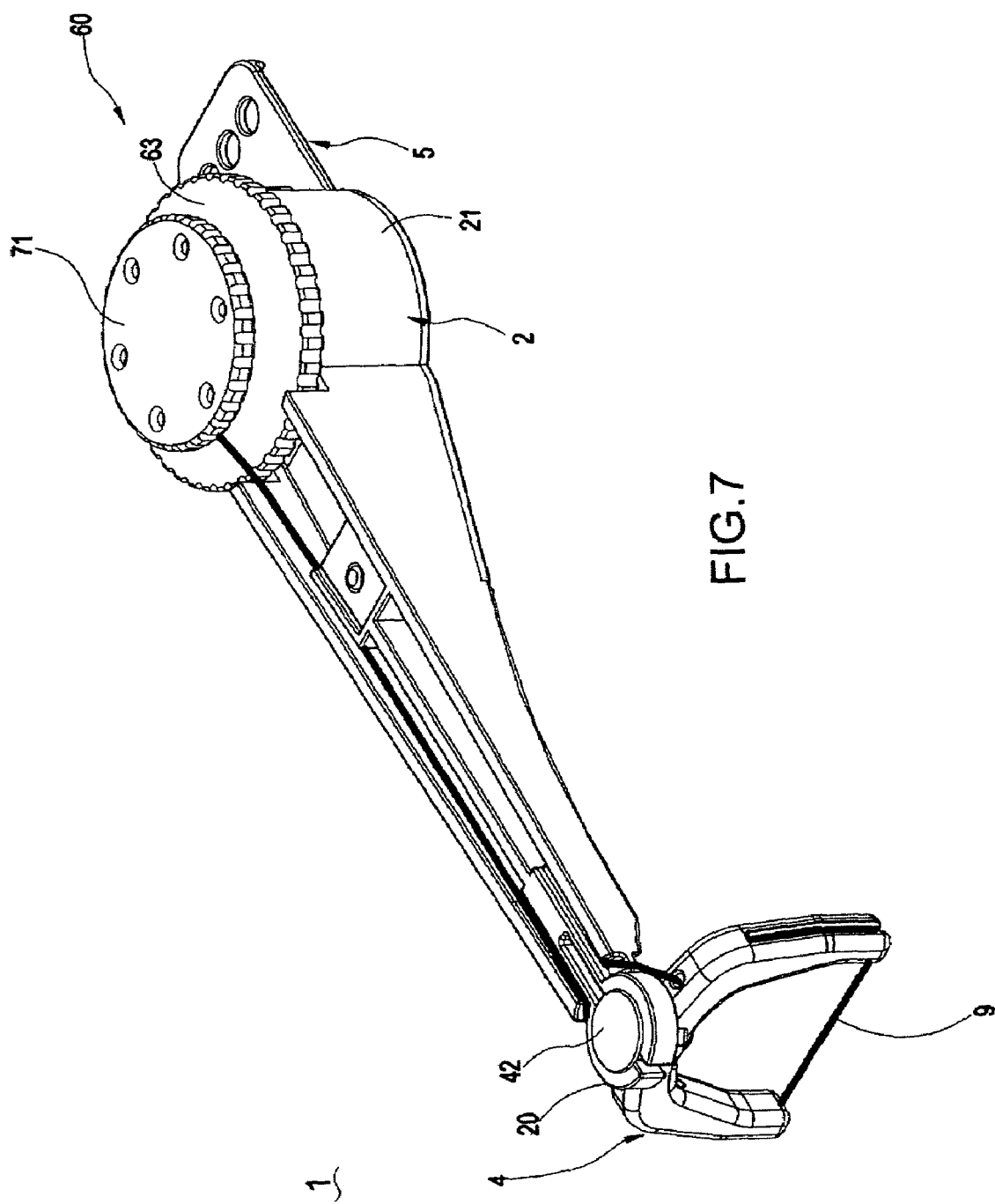
FIG. 7 is a perspective view of fold arms of the dental floss holder turned to different angle.

Referring to FIG. 1, the fork 4 includes a root 40 which defines hollow therein and being mounted on the annular aperture 201, a pair of spaced-apart fork arms 41 extending from the root 40 wherein position holes 410 located on a top of two sides of the fork arms 41 and guiding grooves 411 located along two sides thereof communicating with the position hole 410. The fork arms 41 further have an engaging hole 412 with a smaller diameter than the annular aperture 201 being corresponding to the root 40 (shown as FIG. 2). Moreover, a coaxial column 42 is defined to coaxially mounted to the annular aperture 201 and the root 40; the coaxial column 42 defines a longitudinal cavity 420 thereon and has a first diameter portion 421, a second diameter portion 422 and a third diameter portion 423 which are smaller in sequence. The first diameter portion 421 is fitted into the annular aperture 201, the second diameter portion is fitted into the root 40 and the third diameter portion 423 is fitted into the engaging hole 412 (shown as FIG. 2), wherein the third diameter portion further has a lip fringe 424 extending outwardly from an end thereof for engaging with peripheral fringes of the engaging hole 412. Through aforementioned devices, the fork 4 can be turned directly as shown in FIG. 7, thus different angles of the fork 4 can facilitate cleaning teeth.

The bottom board 5 assembles with a bottom of the housing 2 having the flute 81 mentioned before, a cutter 23 adjacent to a front of the flute 81 for cutting the floss 9 and a hang plate 51 which unitarily extends from a side of the bottom board 5 having a hang hole 52 thereon for hanging the dental floss holder 1.

The sleeve 70 defines hollow axis 701 therein and is fitted into the hollow column 213. The retrieving wheel 71 has a shaft 711 being fitted to the hollow axis 701 and a plurality of threading holes 712 being defined whereon for the floss 9 threading over. In addition, a first driving member 73 and a second driving member 74 are defined arranged between the retrieving wheel 71 and fasten wheel 60 and which are engagable with each other. The first driving member 73 is evenly-spaced arranged on a bottom of the retrieving wheel 71 and projects outwardly there from and the second driving member 74 is arranged on a top of the driving plate 63 corresponding to the first driving member 73 and projects inwardly from the driving plate 63. Accordingly, referring to FIG. 2, when the first driving member 73 engages with the second driving member 74, the retrieving wheel 74 thereby only can turn toward one direction same as the fasten wheel 60.

Through aforementioned devices, with reference to FIG. 1 to FIG. 5, the present dental floss holder 1 in assembly, fit the fork 4 to the annular aperture 201 by coaxially mounting the coaxial column 42, then set the spool 3 with a roll of dental floss 9 on the hollow column 213 of the assembling zone 21, and assemble the slidable plate 80 and the fixing plate 82 with the bottom board 5, fit the fasten wheel 60 on the hollow column 213 and insert the sleeve 70 through the fitting hole 600 of the fasten wheel 60 into the hollow column 213, and then fit the shaft 711 of the retrieving wheel 71 into the hollow axis 701 of the sleeve 70.

Figure 6A:
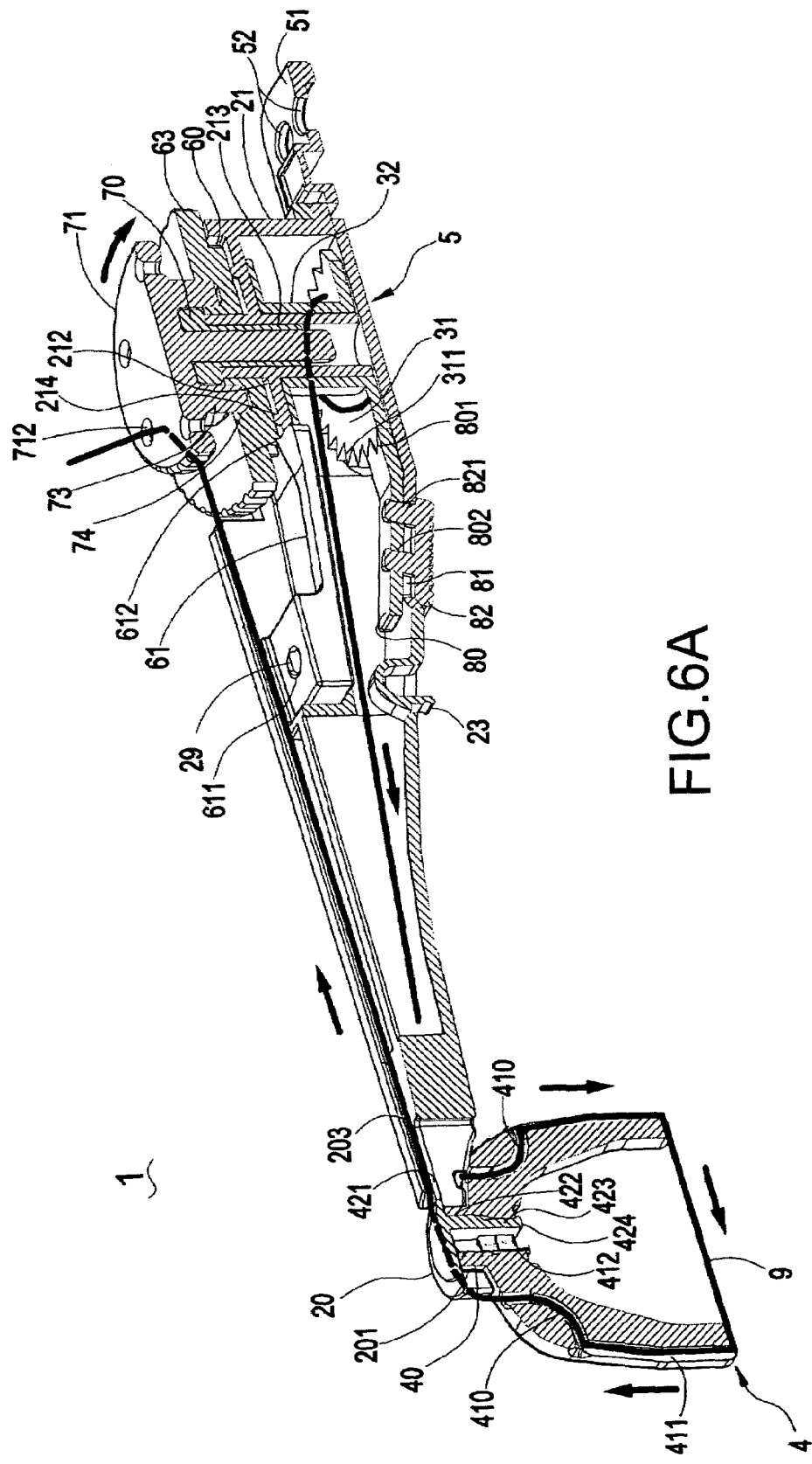
FIG. 6A and FIG. 6B are schematic views of how to thread and fix dental floss in the dental floss holder.
Figure 6B:
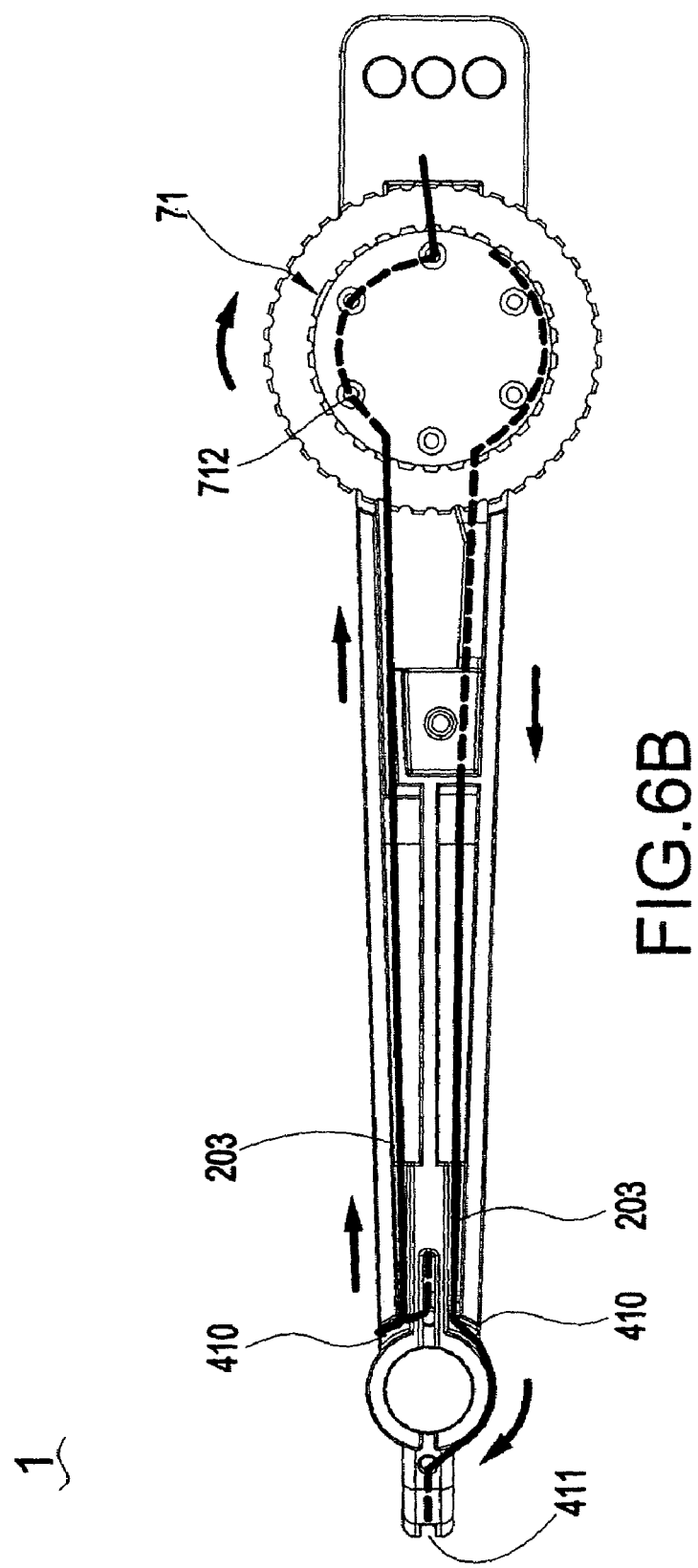

Referring to FIGS. 6A and 6B, in use, an length of the dental floss 9 is drawn from the spool 3 (shown as the direction of arrows) through the leading hole 203 at one side of the housing 2 and the position hole 410 at one side of the fork arms 41, then appropriately thread over the guiding grooves 411 and pass through from another position hole 410 to the leading hole 203 at another side of the housing 2 and the threading holes 712, finally turn the retrieving wheel 71 to tighten up the floss 9. The fork 4 and the housing 2 form as straight after assembling (shown as FIG. 2). When replace the dental floss 9, move the fixing plate 82 toward a reverse direction of the serrated wheel 31, thereby, the saw teeth 801 of the slidable plate 80 is then disengaged from the zigzag recesses 311 of the serrated wheel 31. Accordingly, the spool 3 is available for turning.

To clean molar teeth, only need to turn the fork 4 at right angle. Therefore, the dental floss holder 1 of the present invention is easy to manipulate and to replace the dental floss 9.

It is understood that the invention may be embodied in other forms without departing from the spirit thereof.

What is claimed is:

1. A dental floss holder, comprising:
   a housing having a position base at an end thereof and an assembling zone at another end opposite to the position base, wherein the assembling zone defines a hollow interior forming an upper opening and a lower opening, the upper opening and the lower opening being substantially aligned over one another, the lower opening covered by a bottom board, a partition being defined inside the assembling zone between the upper opening and the lower opening defining an upper compartment and a lower compartment the partition having a hollow column therein, wherein the hollow column is defined transversely perforating the partition;
   a spool including a central tube for holding a roll of dental floss rotatably mounted to the hollow column of the assembly zone in the bottom compartment, said spool further includes a serrated wheel having zigzag recesses on peripheral sides thereof positioned at a side of the central tube adjacent to the bottom board;
   a fasten wheel positioned within the upper opening, having grooves on peripheral sides thereof, the fasten wheel further has a central opening wherein the central opening fits onto the hollow column within the assembly zone;
   a block member located adjacent to said fasten wheel and fixed to said housing; said block member including a pawl which engages the grooves of the fasten wheel for allowing the fasten wheel to move only in one direction;
   a sleeve defining a hollow axis therein and inserted through the central opening of the fasten wheel and into the hollow column to fix the fasten wheel to the assembly zone;
   a retrieving wheel having a top side and a bottom side, a shaft extending from the bottom side and being fitted onto the hollow axis of the sleeve, and a plurality of holes being defined for receiving, a first driving member on said bottom side and a second driving member arranged on a top side of the fasten wheel corresponding to and engaged with the first driving member;
   a fork having a root mounted on the position base, a pair of spaces-apart fork arms extending form the root and position holes located on a top the fork arms.

2. The dental floss holder of claim 1, further including a retaining portion abutting on the assembling zone of the housing for controlling rotation of the spool, which comprises:
   a slidable plate having at least one location hole thereon and defining saw teeth at an end thereof for engaging with the serrated wheel;
   a flute being positioned on the bottom board; and a fixing plate having a peg being mounted into the location hole through the flute.

3. The dental floss holder of claim 2, wherein the position base unitarily and horizontally extends from the assembling zone and said position base formed as an annular ring defining an annular aperture therein for receipt of the root of said fork.

4. The dental floss holder of claim 3, wherein the position base further includes a gap being located through the annular ring for providing elasticity.

5. The dental floss holder of claim 4, wherein further including leading holes being positioned apart at two sides of the housing and opposite to the gap.

6. The dental floss holder of claim 5, wherein the root of the fork defines a hollow opening which is mounted on the annular aperture, and further having an engaging hole with a smaller diameter than the annular aperture being corresponding to the root.

7. The dental floss holder of claim 5, wherein further comprising a coaxial column having a first diameter portion, a second diameter portion and a third diameter portion which are smaller in sequence wherein the first diameter portion being fitted into the annular aperture, the second diameter portion being fitted into the root and the third diameter portion being fitted into the engaging hole.

8. The dental floss holder of claim 7, wherein the third diameter portion has a lip fringe extending outwardly from an end thereof for engaging with peripheral fringes of the engaging hole.

9. The dental floss holder of claim 8, further comprising a cutter located on the bottom board adjacent to a front of the flute.

10. The dental floss holder of claim 9, wherein the partition further has protrusion on the side of the upper opening.

11. The dental floss holder of claim 10, wherein the fork arms further have guiding grooves located along two sides thereof communicating with the position holes.

12. The dental floss holder of claim 11, further comprising a driving plate unitarily formed on top of the fasten wheel which has a larger diameter than the fasten wheel and has ribs on peripheral sides thereof.

13. The dental floss holder of claim 12, wherein the first driving member comprises evenly-spaced projections arranged on the bottom of the retrieving wheel and the second driving member comprises detents on the top of the driving plate corresponding to the projections.

14. The dental floss holder of claim 1, wherein the retrieving wheel further has a plurality of threading holes being arranged thereon.

15. The dental floss holder of claim 1, further including a hang plate unitarily extending from a side of the bottom board having a plurality of hanging holes therein.

* * * * *